United States Patent [19]
Lawlor et al.

[11] Patent Number: 5,422,279
[45] Date of Patent: Jun. 6, 1995

[54] LIPID FRACTIONATION

[75] Inventors: Joseph F. Lawlor, Arlington; Joseph D. Musto, Dover, both of Mass.

[73] Assignee: Reference Diagnostics, Inc., Arlington, Mass.

[21] Appl. No.: 73,532

[22] Filed: Jun. 8, 1993

Related U.S. Application Data

[62] Division of Ser. No. 677,734, Mar. 20, 1991, Pat. No. 5,242,833.

[51] Int. Cl.$^6$ .......................................... G01N 31/02
[52] U.S. Cl. .................... 436/17; 436/177; 436/71; 210/222; 252/62.51
[58] Field of Search ............. 436/526, 177, 166, 17; 210/222, 695; 252/62.51, 62.54

[56] References Cited

U.S. PATENT DOCUMENTS

| | | | |
|---|---|---|---|
| 4,628,037 | 12/1986 | Chagnon et al. | 436/526 |
| 4,661,408 | 4/1987 | Lam et al. | 428/405 |
| 4,687,748 | 8/1987 | Schröder | 436/526 |
| 4,795,698 | 1/1989 | Owen et al. | 435/4 |

(List continued on next page.)

FOREIGN PATENT DOCUMENTS

| | | |
|---|---|---|
| 0125995 | 5/1984 | European Pat. Off. |
| 0230768 | 12/1986 | European Pat. Off. |
| 0247796 | 5/1987 | European Pat. Off. |
| 0317286 | 11/1988 | European Pat. Off. |

(List continued on next page.)

OTHER PUBLICATIONS

Warnick, et al. Clin. Chem. 28/6, 1379–1388 (1982).
Anderson et al., "Particle Distribution of Human Serum High Density Lipoproteins" *Biochem. Biophys. Acta,* vol. 493, pp. 55–68, 1977.
Bachorik et al., "Plasma High-Density Lipoprotein Cholesterol Concentrations Determined after Removal of Other Lipoproteins by Heparin/Manganese Precipitation or by Ultracentrifugation" *Clin. Chem.,* vol. 22, pp. 1828–1834, 1976.
Bachorik et al., "Precipitation Methods for Quantification of Lipoproteins" *Methods Enzymol.,* vol. 129, pp. 78–100, 1986.
Bartl et al., "Turbidimetric kinetic method for serum low density lipoprotein quantitation" *Clin. Chem. Acta,* vol 128, pp. 199–208, 1983.
Burstein et al., "Lipoprotein–Polyanion–Metal Interactions" *Advances in Lipid Research,* vol. 11, pp. 67–108, 1973.
Burstein et al., "Precipitation des Alpha Lipoproteins du Serum Par le Phosphotungstate de Sodium en Presence du Chlorure de Magnesium" *Life Sciences,* vol. 8, pp. 345–348, 1969.
Burstein et al., "Sur un dosage rapide du cholesterol lié aux α-et β-lipoprotéines du sérum" *Clin. Chem. Acts.,* vol. 5, p. 609, 1960.
Cornwell et al., "Molecular complexes in the isolation and characterization of plasma lipoproteins" *J. Lipid Res.,* vol. 2, No. 2, pp. 110–134, Apr. 1961.
Crouse et al., "Studies of low density lipoprotein molecular weight in human beings with coronary artery disease" *J. Lipid Res.,* vol. 26, pp. 566–574, 1985.
Gidez et al., "Separation and quantitation of subclasses of human plasma high density lipoproteins by a simple (List continued on next page.)

*Primary Examiner*—James C. Housel
*Assistant Examiner*—Rachel Heather Freed
*Attorney, Agent, or Firm*—Louis Myers; Lahive & Cockfield

[57] ABSTRACT

A method of separating a first class of lipoprotein in a sample from a second class of lipoprotein in the sample including: precipitating the second class of lipoprotein; contacting the sample with a magnetically responsive particle; and placing the sample in a magnetic field until the magnetically responsive particle has sedimented, thereby causing the precipitated second class of lipoproteins to sediment, leaving the first class of lipoproteins in the supernatant of the sample.

19 Claims, No Drawings

U.S. PATENT DOCUMENTS

| | | | |
|---|---|---|---|
| 4,861,705 | 8/1989 | Margel | 435/2 |
| 4,920,061 | 4/1990 | Poynton et al. | 436/526 |
| 5,076,950 | 12/1991 | Ullman et al. | 252/62.51 |
| 5,242,833 | 9/1993 | Lawlor et al. | 436/71 |

FOREIGN PATENT DOCUMENTS

| | | |
|---|---|---|
| 0343934 | 5/1989 | European Pat. Off. . |
| WO87/02063 | 4/1987 | WIPO . |
| WO88/01744 | 3/1988 | WIPO . |

OTHER PUBLICATIONS precipitation procedure" *J. Lipid Res.*, vol. 23, pp. 1206–1223, 1982.

Gordon et al.,, "High Density Lipoprotein as a Protective Factor Against Coronary Heart Disease" *Am. J. Med.*, vol. 62, pp. 707–714, May 1977.

Gotto, "Lipoprotein Metabolism and the Etiology of Hyperlipidemia" Baylor College of Medicine, pp. 4–13.

Havel et al., "The Distribution and Chemical Composition of Ultracentrifugally Separated Lipoproteins in Human Serum" *J. Clin. Invest.*, vol. 34, pp. 1345–1353, 1955.

Heiss et al., "The Epidemiology of Plasma High-density Lipoprotein Cholesterol Levels" *Circulation*, vol. 62 (Suppl. IV), pp. IV116–IV136, 1980.

Kannel et al., "Cholesterol in the Prediction of Atherosclerotic Disease" *Ann. Intern. Med.*, vol. 90, pp. 85–91, 1979.

Kannel et al., "Optimal Resources for Primary Prevention of Atherosclerotic Diseases" *Circulation*, vol. 70, No. 1, pp. 157A–205A, Jul. 1984.

Kerscher et al., "Precipitation Methods for the Determination of LDL-Cholesterol" *Clin. Biochem.* vol. 18, pp. 118–125, Apr. 1985.

Kohen et al., "Recent advances in chemiluminescence-based immunoassays for steroid hormones" *J. Steriod Biochem.*, vol. 27, Nos. 1–3, pp. 71–79, 1987.

Krauss et al., "Identification of multiple subclasses of plasma low density lipoproteins in normal humans" *J. Lipid Res.*, vol. 23, pp. 97–104, 1982.

Maier et al., "method for the Quantitation of Serum Low Density Lipoprotein Cholesterol" from the American Association for Clinical Chemistry 35th National Meeting in *Clin. Chem.*, vol. 29, p. 1173 (Abstract No. 85), 24–29 Jul. 1983.

McNamara et al., "Effect of Gender, Age, and Lipid Status on Low Density lipoprotein Subfraction Distribution" *Arteriosclerosis*, vol. 7, No. 5, pp. 483–490, Sep.-/Oct. 1987.

Noma et al., "Improved Method for Simultaneous Determination of Cholesterol in High— and Low–Density Lipoproteins" *Clin. Chem.*, vol. 25, No. 8, pp. 1480–1481, 1979.

Noma et al., "Simultaneous Determination of Serum Cholesterol in High— and Low–Density Lipoproteins with Use of Heparin, Ca2+, and an Anion–Exchange Resin" *Clin. Chem.*, vol. 24, No. 9, pp. 1504–1508, 1978.

Shirdi et al., "A direct fluoroimmunoassay for conjugated chenodexycholic acid using antibody coupling to magnetisable particles" *Ann. Clin. Biochem.*, vol. 17, pp. 181–191, 1980.

Viikari, "Precipitation of Plasma Lipoproteins by PEG–6000 and its Evaluation with Electrophoresis and Ultracentrifugation" *Scand. J. Clin. Lab Invest.*, vol. 36, pp. 265–268, 1976.

Walton et al., "Estimation of the low–density (beta) lipoproteins of serum in health and disease using large molecular weight dextran sulphate" *J. Clin. Path.*, pp. 17, 627–643, 1964.

Warnick et al., "A comprehensive evaluation of the heparin–managanese precipitaiton procedure for estimating high density lipoprotein cholesterol" *J. Lipid Res.*, vol. 19, pp. 65–76, 1978.

Warnick et al., "Dextran Sulfate-Mg2+ Precipitation Procedure for Quantitation of High–Density–Lipoprotein Cholesterol" *Clin. Chem.*, vol. 28, No. 6, pp. 1379–1388, 1982.

Whitaker et al., "Simplified Methods for Measuring Cholesterol Concentrations of High–Density Lipoprotein Subclasses in Serum Compared" *Clin. Chem.*, vol. 32, No. 7, pp. 1274–1278, 1986.

Wieland et al., "A simple specific method for precipitation of low density lipoproteins" *J. Lipid Res.*, vol. 24, pp. 904–909, 1983.

Fredrickson et al., "A Comparison of Heritable Abnormal Lipoprotein Patterns As Defined by Two Different Techniques" *J. Clin. Inv.*, vol. 47, pp. 2446–2457.

Warnick et al., "Heparin–Mn2+ Quantitation of High-–Density–Lipoprotein Cholesterol: An Ultrafiltration Procedure for Lipemic Samples" *Clin. Chem.*, vol. 24, No. 6, pp. 900–904.

LIPID FRACTIONATION

This application is a divisional of U.S. patent application Ser. No. 07/677,734, filed Mar. 20, 1991, entitled LIPID FRACTIONATION, now U.S. Pat. No. 5,242,833.

BACKGROUND OF THE INVENTION

This invention relates to the fractionation of lipid mixtures.

Plasma lipoproteins are spherical particles which contain varying amounts of cholesterol, triglycerides, phospholipids, and proteins. They include an outer surface composed of phospholipid, free cholesterol, and protein, and an inner core containing mostly esterified cholesterol and triglycerides. Plasma lipoproteins serve to solubilize and transport cholesterol and triglyceride in the bloodstream.

The relative proportion of protein and lipid in a plasma lipoprotein determines the density of the plasma lipoprotein, Gotto, 1988, *Hosp. Pract.* 23:4 (Suppl. 1). Based on their density, particle size, composition, and electrophoretic mobility, circulating lipoproteins have been categorized into four major classes. The classes are: chylomicrons, very-low-density lipoproteins (VLDL), low-density lipoproteins (LDL), and high-density lipoproteins (HDL). Some of the characteristics of these classes are shown in Table 1.

TABLE 1
CHARACTERISTICS OF PLASMA LIPOPROTEINS

| | Diameter (Angstroms) | Density (g/ml) | Origin |
|---|---|---|---|
| Chylomicrons | 750–12,000 | <0.95 | intestine |
| VLDL | 300–700 | <1.006 | liver |
| LDL | 180–300 | 1.019–1.063 | catabolism of VLDL |
| HDL | 50–120 | 1.063–1.21 | liver & intestine |

The major classes of lipoproteins can be further divided into subclasses. LDL includes at least 7 subclasses, as is described in McNamara, 1990, *AACC Lipids and Lipoproteins Division Newsletter* 4:1, hereby incorporated by reference, Krauss et al., 1982, *J. Lipid Res.* 23:97, hereby incorporated by reference, and McNamara et al., 1987, *Arteriosclerosis* 7:483, hereby incorporated by reference. HDL includes at least two subclasses, $HDL_2$ and $HDL_3$, as is described in Whitaker, 1986, *Clin. Chem.* 32:1274, hereby incorporated by reference and Anderson, 1977, *Biochim. Biophys. Acta* 493:55, hereby incorporated by reference.

The major risk factors for coronary heart disease are hypercholesterolemia, cigarette smoking, hypertension, diabetes, obesity, and male sex. Although hypercholesterolemia in general is the most prominent of these risk factors, numerous clinical studies have shown that the different lipoprotein classes have very distinct and varied effects on heart disease, Crouse et al., 1985, *J. Lipid Res.*, 26:566–572; Kannel et al., 1979, *Ann. Intern. Med.*, 90:85–91; Kannel et al., 1984, *Circulation* 70:157A–205A. In fact the presence of HDL provides a protective effect against coronary heart disease, and therefore relatively low HDL-cholesterol levels may be indicative of greater risk, Miller et al., 1975, *Lancet* 16:23; Castelli et al., 1977, *Circulation* 55:767; Gordon et al., 1977, *Am. J. Med.* 62:707; Heis et al., 1980 *Circulation* 62:116 (Suppl. 4).

Recognition of the importance of HDL cholesterol as a strong inverse risk factor for coronary artery disease has led to substantial demand for an HDL cholesterol assay suitable for clinical and research use. Various methods, including ultracentrifugation, electrophoresis, and specific precipitation, Havel et al., 1955, *J. Clin. Invest.* 34:1345, have been used to separate various classes of lipoproteins.

Precipitation-based methods have been used widely for routine quantitation of lipoproteins. Several precipitation-based methods have been described in the recent literature. Most of these methods are based on earlier work by Burstein and colleagues (reviewed in Burstein, M., and Scholnick, J. R., Lipoprotein-polyanion-metal interactions, In, *Advances in Lipid Research* 11, R. Paoletti and D. Kritchevsky, Eds., Academic Press, New York, N.Y. 1973, pp. 67–108). In these methods, the fractionation of lipoproteins in a solution, e.g., serum, is accomplished primarily by selective precipitation followed by centrifugation. The supernatant is then used to determine the cholesterol content remaining, or, by difference, the cholesterol content of that fraction which has been specifically removed from the supernatant. For example, low density lipoprotein (LDL) cholesterol, can be determined in this manner by specifically precipitating only LDL using heparin in citrate buffer at pH 5.04. Others have reported using polyvinyl sulfate or polyethylene glycol to effect specific precipitation of LDL and VLDL. In each case, centrifugation is necessary before measuring the cholesterol content.

Similarly, the measurement of HDL-cholesterol is usually a two-step process in which HDL is first separated from the other apoB-containing plasma lipoproteins, and the cholesterol content of the HDL-containing fraction measured. The most commonly employed methods are based on those developed by Burstein and his colleagues (Burstein et al., 1988, in Clarkson TB, Kritchevsky D, Pollak OJ (eds): *Monographs on Atherosclerosis*, New York, Karger) in which the apoB-containing lipoproteins are removed by precipitation with a polyanion in combination with a divalent cation, Bachorik et al., 1986, *Methods Enzymol.* 129:78. The two most commonly used precipitants are sodium phosphotungstate-$MgCl_2$ and dextran sulfate (m.wt. 50,000)-$MgCl_2$, Warnick et al., 1982, *Clin. Chem.* 23:1379. Other precipitants used include heparin sulfate-$MnCl_2$ and heparin sulfate-calcium carbonate. In these assays the precipitating reagent is added to an aliquot of serum or plasma. A heavy white precipitate forms immediately, and the mixture is allowed to stand until precipitation is complete. The precipitate is then sedimented by centrifugation, and an aliquot of the clear supernatant is removed for cholesterol analysis.

The first method used extensively in major population studies employed heparin and $Mn^{++}$ to precipitate VLDL and LDL, allowing HDL to be measured in terms of the amount of cholesterol remaining in the supernatant solution, Burstein et al., 1960, *Clin. Chim. Acta* 5:609, Frederickson et al., 1968, *J. Clin. Invest.* 47:2446–2457, *Manual of Laboratory Operations, Lipid Research Clinics Program, Lipid and Lipoprotein Analysis,* I. National Heart and Lung Institute. DHEW Publications No. (NIH) 75–628, 1974. This method has been extensively studied, Bachorik et al., 1976, *Clin. Chem.* 22:1828–1834, Warnick et al., 1978a, *J. Lipid Res.* 19:65–76, and modifications have been described, Warnick et al., 1978a, supra; Warnick et al., 1978b, *Clin. Chem.* 24:900.

SUMMARY OF THE INVENTION

In general, the invention features a method of separating a first class of lipoprotein, e.g., any of HDL, LDL, or VLDL, in a sample from a second class of lipoprotein, e.g., any or all of the remaining types of lipoproteins in the sample, e.g., separating HDL from LDL and/or VLDL, separating LDL from HDL and/or VLDL, or separating VLDL from LDL and/or HDL. The method includes: precipitating the second class of lipoprotein, preferably by contacting the sample with a precipitating reagent; contacting the sample with a magnetically responsive particle; and placing the sample in a magnetic field until the magnetically responsive particles have sedimented, thereby causing the precipitated second class of lipoproteins to sediment and leaving the first class of lipoproteins in the supernatant of the sample.

Preferred embodiments include those in which the precipitating reagent is contacted with the sample prior to contacting the sample with the magnetically responsive particles; the precipitating reagent and the magnetically responsive particles are contacted with the sample simultaneously, i.e., they are added simultaneously; the precipitating reagent includes e.g., dextran sulfate and $MgCl_2$, or phosphotungstic acid and $MgCl_2$; the magnetically responsive particles include polyacrolein and a form of iron e.g., iron oxide; the sample contains up to 1,300 mg/dl triglycerides; the sample is a biological fluid, e.g., blood, plasma, or serum, from an animal, e.g, a vertebrate, e.g., a mammal, e.g., a human; the sample will not be returned to an animal; and the sample will be returned to an animal e.g., the animal from which the sample was taken.

In another aspect the invention features a method of measuring the amount of a constituent, e.g., cholesterol, phospholipid, apolipoprotein, triglyceride, or cholesterol ester, contained in a first class of lipoprotein, e.g., HDL, LDL, or VLDL in a sample. The sample includes a first and a second class of lipoprotein, the second class including any other class of lipoprotein, e.g., if the first class is HDL, the second class can be LDL, VLDL, or both. The method includes: precipitating the second class of lipoprotein, preferably by contacting the sample with a precipitating reagent; contacting the sample with a magnetically responsive particle; placing the sample in a magnetic field until the magnetically responsive particles have sedimented, thereby causing the precipitated second class of lipoproteins to sediment, leaving the first class of lipoproteins in the supernatant of the sample; and determining the amount of cholesterol in the first class of lipoprotein.

Preferred embodiments include those in which the amount of the constituent of interest in the first class is determined by determining the amount of the constituent in the supernatant, and those in which the amount of the constituent in the first class is determined by determining the total amount of the constituent present in the sample, determining the amount of the constituent in the sedimented second class, and subtracting the latter from the former.

Preferred embodiments include those in which: the precipitating reagent is contacted with the sample prior to contacting the sample with the magnetically responsive particles; the precipitating reagent and the magnetically responsive particles are contacted with the sample simultaneously, i.e., they are added simultaneously to the sample; the precipitating reagent includes e.g., dextran sulfate and $MgCl_2$, or phosphotungstic acid and $MgCl_2$; the magnetically responsive particles include polyacrolein and a form of iron, e.g., iron oxide; the sample contain up to 1,300 mg/dl triglycerides; the sample is a biological fluid, e.g., blood, plasma, or serum, from an animal, e.g., a vertebrate, e.g., a mammal, e.g., a human; the measurement is performed on an automated device; and the measurement is performed on a manually operated spectrophotometer.

Preferred embodiments include those in which the concentration of a constituent, e.g., cholesterol, phospholipid, apolipoprotein, triglyceride, or cholesterol ester, in the HDL of a sample is determined by precipitating and sedimenting the LDL and VLDL in the sample, then measuring the concentration of the constituent in the supernatant; the concentration of a constituent, e.g., cholesterol, phospholipid, apolipoprotein, triglyceride, or cholesterol ester, in the LDL of a sample is determined by precipitating and sedimenting the HDL and VLDL in the sample, then measuring the concentration of the constituent in the supernatant; the concentration of a constituent, e.g., cholesterol, phospholipid, apolipoprotein, triglyceride, or cholesterol ester, in the VLDL of a sample is determined by precipitating and sedimenting the LDL and HDL in the sample, then measuring the concentration of the constituent in the supernatant; the concentration of a constituent, e.g., cholesterol, phospholipid, apolipoprotein, triglyceride, or cholesterol ester, in the HDL of a sample is determined by precipitating and sedimenting the LDL and VLDL in the sample, determining the amount of the constituent in the sediment, determining the total amount of the constituent in the sample, then subtracting the former from the latter; the concentration of a constituent, e.g., cholesterol, phospholipid, apolipoprotein, triglyceride, or cholesterol ester, in the LDL of a sample is determined by precipitating and sedimenting the HDL and VLDL in the sample, determining the amount of the constituent in the sediment, determining the total amount of the constituent in the sample, then subtracting the former from the latter; and the concentration of a constituent, e.g., cholesterol, phospholipid, apolipoprotein, triglyceride, or cholesterol ester, in the VLDL of a sample is determined by precipitating and sedimenting the HDL and LDL in the sample, determining the amount of the constituent in the sediment, determining the total amount of the constituent in the sample, then subtracting the former from the latter.

The invention also includes a method of measuring the amount of a constituent, e.g., cholesterol, phospholipid, apolipoprotein, triglyceride, or cholesterol ester, contained in a first class of lipoprotein, e.g., HDL, or LDL, or VLDL, in a sample. The sample includes a first and a second class of lipoprotein, wherein the second class of lipoprotein can include any other class of lipoprotein, e.g. if the first class is HDL, the second class can be LDL, or VLDL, or both. The method includes: precipitating the first class of lipoprotein, preferably by contacting the sample with a precipitating reagent; contacting the sample with magnetically responsive particles; placing the sample in a magnetic field until the magnetically responsive particles have sedimented, thereby causing the precipitated first class of lipoproteins to sediment, leaving the second class of lipoproteins in the supernatant of the sample; and determining the amount of cholesterol in the first class of lipoprotein.

Preferred embodiments include those in which the amount of the constituent of interest in the first class is determined by determining the amount of the constituent in the sedimented first class, and those in which the amount of the constituent in the first class is determined by determining the total amount of the constituent present in the sample, determining the amount of the constituent in the supernatant, and subtracting the latter from the former.

Preferred embodiments include those in which the precipitating reagent is contacted with the sample prior to contacting the sample with the magnetically responsive particle; the precipitating reagent and the magnetically responsive particles are contacted with the sample simultaneously, i.e., they are added to the sample simultaneously; the precipitating reagent includes e.g., dextran sulfate and $MgCl_2$, polyethylene glycol, heparin and citrate, or phosphotungstic acid and $MgCl_2$; the magnetically responsive particles include polyacrolein and a form of iron, e.g., iron oxide; the sample contains up to 1,300 mg/dl triglycerides; the sample is a biological fluid, e.g., blood, plasma, or serum, from an animal, e.g, a vertebrate, e.g., a mammal, e.g., a human; the measurement is performed on an automated device; and the measurement is performed on a manually operated spectrophotometer.

Preferred embodiments include those in which the level of a constituent, e.g., cholesterol, phospholipid, apolipoprotein, triglyceride, or cholesterol ester, in the LDL of a sample is determined by precipitating and sedimenting the LDL in the sample, then measuring the level of the constituent in the sediment; the level of a constituent, e.g., cholesterol, phospholipid, apolipoprotein, triglyceride, or cholesterol ester, in the VLDL of a sample is determined by precipitating and sedimenting the VLDL in the sample, then measuring the level of the constituent in the sediment; the level of a constituent, e.g., cholesterol, phospholipid, apolipoprotein, triglyceride, or cholesterol ester, in the HDL of a sample is determined by precipitating and sedimenting the HDL in the sample, then measuring the level of the constituent in the sediment; the level of a constituent, e.g., cholesterol, phospholipid, apolipoprotein, triglyceride, or cholesterol ester, in the LDL of a sample is determined by precipitating and sedimenting the LDL in the sample (leaving the HDL and VLDL in the supernatant), determining the amount of the constituent in the supernatant, determining the total amount of the constituent in the sample, then subtracting the former from the latter; the level of a constituent, e.g., cholesterol, phospholipid, apolipoprotein, triglyceride, or cholesterol ester, in the HDL of a sample is determined by precipitating and sedimenting the HDL in the sample, (leaving the LDL and VLDL in the supernatant) determining the amount of the constituent in the supernatant, determining the total amount of the constituent in the sample, then subtracting the former from the latter; and the level of a constituent, e.g., cholesterol, phospholipid, apolipoprotein, triglyceride, or cholesterol ester, in the VLDL of a sample is determined by precipitating and sedimenting the VLDL (leaving the LDL and HDL in the supernatant) in the sample, determining the amount of the constituent in the supernatant, determining the total amount of the constituent in the sample, then subtracting the former from the latter.

A class of lipoprotein, as used herein, can refer to one of the major classes of lipoprotein, e.g., HDL, LDL, or VLDL, or one of the subclasses of the major classes, e.g., one of the seven subclasses of the LDL major class or one of the two subclasses of the HDL major class.

Methods of the invention use magnetically responsive particles for the rapid removal of lipoproteins that have been selectively precipitated from an aqueous medium such as blood, plasma, or serum. Preferred embodiments provide enhanced fractionation by selective precipitation of lipoproteins of one or more classes (e.g., any of HDL, LDL or VLDL) coupled with magnetically induced sedimentation. Fractionation is an important step in the measurement of pathologically significant lipid components such as HDL cholesterol, LDL cholesterol, and VLDL cholesterol.

The use of magnetizable particles eliminates or reduces the need for a centrifugation step in plasma lipoprotein fractionation. As a result, magnetically based separations are relatively rapid, do not require expensive or energy consuming equipment, and reduce radiological, biological, and physical hazards. Furthermore, samples are not exposed to centrifuge-generated heat, which can compromise the integrity of the samples.

Methods of the invention allow for complete sedimentation of precipitated lipoproteins without additional dilution of the sample, even in samples with high concentrations of triglycerides. Thus, the time and expense required for diluting samples, and errors in estimation that arise from dilution, are eliminated.

Magnetic separation methods of the invention can be incorporated into an automated clinical analyzer (of the type commonly used for cholesterol measurements) to allow in-line separation and direct automated measurement of HDL-cholesterol, and/or LDL-cholesterol, and/or VLDL-cholesterol.

The magnetic separation methods of the invention can be used in the measurement of any lipoprotein component, e.g., phospholipids, triglycerides, apolipoproteins, or cholesterol esters, found in a class of lipoprotein.

Other features and advantages of the invention will be apparent from the following description of the preferred embodiments, and from the claims.

DESCRIPTION OF THE PREFERRED EMBODIMENTS

Reagents

A "magnetically responsive particle" or "magnetic particle", as used herein, is any particle dispersable or suspendable in aqueous media and separable from suspension by application of a magnetic field. This includes particles that are intrinsically magnetically responsive or particles that have been rendered magnetically responsive, e.g., by attachment to a magnetically responsive substance or by incorporation of such substance into the particles. The magnetic component can be incorporated into a particle e.g., by impregnating the substance in a polymeric matrix such as cellulose or polyacrolein. The magnetic particles can be ferromagnetic, superparamagnetic, or more preferably paramagnetic.

The magnetic component of magnetically responsive particles can be any component that is susceptible to a magnetic field, e.g., salts, oxides, brides, or sulfides of iron, cobalt, or nickel; rare earth elements having high magnetic susceptibility, e.g., hematite or ferrite; or pure magnetically responsive metals or alloys thereof. A wide variety of particles e.g., cellulose/iron oxide or polyacrolein/iron oxide, are suitable for use in the invention.

Magnetic particles can be obtained from Cortex Biochem., Inc., (San Leandro, Calif.). Several types of magnetic particles were tested. They are, in order of descending preference, polyacrolein/iron oxide (e.g., Cortex #CM1001), cellulose/iron oxide (e.g., Cortex #CM1000), low density cellulose/iron oxide (e.g., Cortex #CM1003), and magnetizable charcoal (e.g., Cortex #CM5002).

Methods for the fabrication of magnetically responsive particles are known to those skilled in the art, see e.g., U.S. Pat. No. 4,628,037, hereby incorporated by reference, which discloses the production of particles with magnetic metal oxide cores; U.S. Pat. No. 4,687,748, hereby incorporated by reference, which discloses the preparation of spheres composed of magnetic particles included in a polymer matrix, e.g., in a carbohydrate matrix; U.S. Pat. No. 4,795,698, hereby incorporated by reference, which discloses the production of magnetic-polymer particles by the coprecipitation of transition metals in the presence of a polymer having available coordination sites; and U.S. Pat. No. 4,661,408, hereby incorporated by reference, which discloses the preparation of magnetically responsive particles with a core of $CrO_2$. Magnetically responsive particles are also commercially available, as described herein.

The magnetically responsive particles may be added sequentially or simultaneously with the precipitating reagent. If added simultaneously, (using a single precipitation/magnetically responsive particle reagent) the size and surface characteristics should be chosen to allow the particles to remain in suspension until the precipitation is complete—at which time magnetic separation is applied. For this type of "simultaneous addition" procedure, particles in the range of 1-10 microns have been used for selective lipoprotein precipitation assays.

Magnetically responsive particles smaller than 1 micron will also work well since they are likely to remain in suspension until the magnetic field is applied. The upper limit of particle size depends on factors which, in addition to size, determine sedimentation rate in the absence of a magnetic field e.g., particle density, the nature of the functional groups on the surface of the particle (e.g., hydrophilic groups would result in relatively slower sedimentation while hydrophobic groups would result in more rapid sedimentation), and on the rate of reaction for the specific lipoprotein precipitation reaction being used. The particles must remain in suspension long enough to allow precipitation of the desired lipoprotein.

Factors affecting the choice of size of a magnetically responsive particle are known to those skilled in the art., see e.g., European Patent Application No. 86309967.7, hereby incorporated by reference; U.S. Pat. No. 4,628,037, hereby incorporated by reference; U.S. Pat. No. 4,687,748, hereby incorporated by reference.

The reagent used for the specific lipoprotein precipitation will vary with the lipoprotein to be precipitated and can be chosen by methods known to those skilled in the art. Heparin and citrate, heparin-$Mn^{++}$, dextran sulfate-$Mg^{++}$, polyethyleneglycol, polyethylene glycol-polyvinyl sulfate, and phosphotungstate-$Mg^{++}$ have all been used successfully for selective precipitation of one or more class of lipoproteins.

Precipitating reagents useful in the analysis of HDL-cholesterol are known to those skilled in the art and include the following: heparin/$Mn^{++}$ (available e.g., from WAKO Chemicals, Dallas, Tex.) (Burstein et al., 1960, supra, Warnick et al., 1978, J. Lipid. Res. 19:65, hereby incorporated by reference); phosphotungstic acid/$MgCl_2$ (available e.g., from Sigma Chemical or Roche Diagnostics) (Drager et al., 1982 Lab. Med. 6:198, hereby incorporated by reference, Burstein et al., 1969, Life Sci. 8:345, hereby incorporated by reference); dextran-$SO_4$/$MgCl_2$ (available e.g, from DMA) (Warnick et al., 1982, Clin. Chem. 28:1379, hereby incorporated by reference); heparin/$MgCl_2$/sucrose; (Burstein, 1962, C. R. Acad. Sci. 225:605, hereby incorporated by reference); Heparin/$Ca^{++}$ (Noma et al., 1978, Clin. Chem. 24:150, hereby incorporated by reference); heparin/$Ca^{++}$/$Ni^{++}$ (Noma et al., 1979, Clin. Chem. 25:1480, hereby incorporated by reference); or polyethylene glycol, (available e.g., from Diagnostic Chemicals Ltd., Monroe, Conn.) (Vikari, 1976, J. Clin. Lab. Invest. 36:265 hereby incorporated by reference).

Subclasses of HDL can be separated from one another and from other classes of lipoprotein, see e.g., Whitaker et al., 1986, Clin. Chem. 32.:1274, hereby incorporated by reference, or Gidez et al., 1982, J. Lipid. Res. 23:1206, hereby incorporated by reference.

Precipitating reagents useful in the analysis of LDL-cholesterol are known to those skilled in the art and include the following: heparin and titrate (available from Genzyme, One Kendall Square, Cambridge, Mass. or E. Merck, A.G. (Germany) as LDL cholesterin Cat. No. 14992) (Wieland et al., 1983, J. Lipid Res. 24:904, hereby incorporated by reference); polyvinylsulfate, (available from Boehringer, Mannheim (FRG) as LDL-cholesterol Cat. No. 726290) (Assmann et al., 1984, Clin. Chem. Acta 140:77, hereby incorporated by reference, Maier et al., 1983, Clin. Chem. 29:1173, hereby incorporated by reference, Kerscher et al., 1985, Clin. Biochem. 18:118, hereby incorporated by reference); PVS/PEGME (polyvinyl sulfate polyethyleneglycol methyl ether) (available from BioMerieux, Cat. No. 61532, 69260 Charbonnieres, France) (Wehmeyer et al., Abstract Presented at 1983 national meeting of Am. Assoc. for Clin. Chemistry, Boehringer Mannheim, GmbH, Research Center, Tutzing, Germany); heparin/$Ca^{++}$/EDTA/liPase (Bartl et al., 1983, Clin. Chem. Acta 128:199, hereby incorporated by reference); dextran $So_4$/$Ca^{++}$ (available from Immuno A.G. Vienna, Austria as Quantolip LDL-cholesterol) (Walton et al., 1964, J. Clin. Path. 17:627, hereby incorporated by reference, Cornwell et al., 1961, J. Lipid Res. 2:110, hereby incorporated by reference); heparin/resin (Noma et al., 1978, Clin. Chem. 24:1504, hereby incorporated by reference).

For each specific precipitation reagent one or more types of magnetically responsive particle can be applied over a wide range of particle concentrations, e.g., phosphotungstate or dextran sulfate can be used to precipitate LDL and VLDL, leaving HDL in the supernatant solution. With either of these reagent systems many magnetically responsive particles work well in a "sequential addition" mode, i.e., wherein the precipitating reagent is added first and the magnetically responsive particles are added after allowing precipitation to take place. Several also perform satisfactorily in the "simultaneous addition" mode, i.e., wherein the precipitating reagent and the magnetic particles are added simultaneously. Reagents, however, may be added in any sequence which results in effective precipitation and sedimentation.

The concentration of magnetically responsive particle needed to effect rapid complete separation will vary, e.g., with the concentration of lipid in the sample. The concentration for a given application can be determined by methods known to those skilled in the art and as described herein. In many cases the concentration of magnetically responsive particles in the reagent mixture will vary from 5 to 50 mg/ml and more preferably the concentration will vary from 15-25 mg/ml.

The precipitating reagent can be bound, by methods known to those skilled in the art, to the surface of the magnetically responsive particles, to enhance stability, lot-to-lot consistency, or to assure even faster separation, but the use of magnetically responsive particles to provide rapid, efficient separation usually does not require that the precipitating reagent be bound to the magnetic particles.

EXAMPLE 1

Comparison of Magnetic Particle-Based Sedimentation with a Centrifuge-Based Method for the Determination of HDL Cholesterol Content of Serum In this example magnetic particle-based separation methods of the invention were compared with a method in which centrifugation was used to sediment the precipitated lipoproteins. In all cases lipoproteins were precipitated with dextran $SO_4/MgCl_2$.

Magnetic particles and precipitating reagent were combined to form a combined magnetic particle-/precipitating reagent. Magnetic particles were added to the combined reagent as a 50 mg/ml slurry of particles in water. 100 ml of combined magnetic particle precipitating reagent included between 10 and 50 ml of slurry, 50 mls. of dextran sulfate-$MgCl_2$, and water (if needed) to make 100 ml. The dextran sulfate-$MgCl_2$ solution was purchased from DMA or was formulated according to the method of Warnick et al., 1982, Clin. Chem. 28:1374, hereby incorporated by reference, from commercially available material. The data in Table 2 was obtained with dextran sulfate-$MgCl_2$ obtained form DMA. In the magnetic separations shown in Table 2, 0.1 mls of the combined precipitation reagent/magnetic particle reagent (50 ml magnetic particle slurry/100 ml combined reagent) was added to a 0.50 ml serum sample and allowed to incubate for 10 min. (Later experiments show that 1 min. of incubation is sufficient.) Samples to be magnetically sedimented were placed in a Serono Diagnostics magnetic rack for 1-10 min. (Usually 1-3 min. is sufficient.)

Magnetic particles were obtained from Cortex Biochem., Inc. (San Leandro, Calif.). Four types of particles were tested: M-1, M-2, M-3, and M-4. M-1 refers to Low Density Cellulose/iron oxide (#CM1004) (1-10 μ in diameter); M-2 refers to Cellulose/iron oxide (#CM1000) (1-10 μ in diameter); M-3 refers to Polyacrolein/iron oxide (#CM1001) (1-10 μ in diameter); M-4 refers to Magnetizable charcoal (#CM5002) (1-25 μ in diameter).

For centrifuged samples, 0.05 ml of precipitating reagent was added to a 0.50 ml sample, allowed to stand for 10 minutes and then spun at 2000 rpm for 15 min. in a standard laboratory centrifuge. Total cholesterol in the supernatants (which is equivalent to HDL cholesterol) was analyzed by standard methods, and results expressed as mg/dl of cholesterol.

The results are shown in Table 2.

TABLE 2

| | METHOD OF SEPARATION | | | | |
|---|---|---|---|---|---|
| | Centrifugal | Magnetic Separation | | | |
| Patient No. | Separation | M-1 | M-2 | M-3 | M-4 |
| 1. | 39,38 | 38,39 | 39,40 | 39,39 | 44,48 |
| 2. | 42,43 | 41,41 | 40,41 | 42.5,42.5 | N.G. |
| 3. | 63,59 | 58,58 | 57,58 | 55,57 | N.G. |
| 4. | 43,43 | — | 45,46 | 46,47 | — |
| 5. | 31,31 | — | 34,34 | 32,34 | — |
| 6. | 34,34 | — | 36,37 | 36,36 | — |
| 7. | 36,37 | — | 37,37 | 36,37 | — |
| 8. | 45,49 | — | 48,48 | 47,49 | — |
| 9. | 46,47 | — | 47,49 | 47,50 | — |
| 10. | 51,52 | — | 50,51 | 51,51 | — |
| 11. | 47,48 | — | 44,46 | 44,44 | — |
| 12. | 43,43 | — | 43,44 | 45,45 | — |
| 13. | 44,44 | — | 44,45 | 44,46 | — |
| 14. | 51,52 | — | 53,55 | 53,55 | — |
| 15. | 35,35 | — | 35,35 | 36,36 | — |
| 16. | 41,42 | — | 48,48 | 40,41 | — |
| 17. | 42,42 | — | 34,34 | 41,43 | — |
| 18. | 28,28 | — | 26,29 | 31,32 | — |
| 19. | 62,62 | — | 60,60 | 59,60 | — |
| 20. | 48,48 | — | 38,39 | 47,48 | — |
| 21. | 51,51 | — | 51,59 | 53,51 | — |
| 22. | 33,33 | — | 34,34 | 33,33 | — |

EXAMPLE 2

Amount of Magnetic Particles Required

The amount of magnetic particles needed for reliable results was determined by comparing the HDL-cholesterol values obtained in a centrifugation based assay with values obtained in magnetic separation using differing amounts of polyacrolein/iron oxide particles. The amount of particles was varied by varying the amount of slurry added to 100 ml of combined reagent, as described above. 0.10 ml of combined reagent was added to 0.50 ml of sample. All other materials and methods are described in Example 1. The results are shown in Tables 3 and 4. The results are expressed as mg/dl HDL cholesterol.

TABLE 3

| | METHOD OF SEPARATION | | | | | |
|---|---|---|---|---|---|---|
| | | Magnetic Separations Volume of slurry | | | | |
| Patient | Centrifugal | (as % of combined reagent volume) | | | | |
| No. | Separations | 50% | 40% | 30% | 20% | 10% |
| 1 | 69 | 74 | 67 | 68 | 68 | — |
| 2 | 72 | 73 | 70 | 72 | 70 | — |
| 3 | 53 | 54 | 49 | 50 | 51 | — |
| 4 | 48 | 50 | 48 | 47 | 48 | — |
| 5 | 44 | 48 | 43 | 42 | 44 | — |
| 6 | 41 | 40 | 40 | 37 | 42 | — |
| 7 | 44 | 42 | 43 | 44 | 46 | — |
| 8 | 96 | 91 | 92 | 91 | 96 | — |
| 9 | 43 | 40 | 52 | 43 | 43 | — |
| 10 | 41 | 39 | 40 | 42 | 42 | — |
| 11 | 36 | 33 | 35 | 36 | 36 | — |
| 12 | 30 | 28 | — | 32 | 32 | — |
| 13 | 57 | 54 | 57 | 56 | 58 | — |
| 14 | 37 | 33 | 38 | 35 | 37 | — |
| 15 | 85 | 80 | 83 | 82 | 84 | — |
| 16 | 82 | 78 | 80 | 79 | 82 | — |
| 17 | 51 | 49 | — | 51 | 51 | — |
| 18 | 50 | 49 | 50 | 54 | 52 | — |
| 19 | 48 | 46 | 46 | 49 | 49 | — |
| 20 | 51 | 47 | 50 | 49 | 50 | — |
| 21 | 38 | 38 | 37 | 40 | 38 | — |
| 22 | 51 | 49 | 50 | 40 | 52 | — |
| 23 | 50 | 49 | 48 | — | 52 | — |

TABLE 4

| | METHOD OF SEPARATION | | | | |
|---|---|---|---|---|---|
| | | Magnetic Separations Volume of slurry (as % of combined reagent volume) | | | |
| Patient No. | Centrifugal Separations | 15% | 17.5% | 20% | 22.5% |
| 1 | 23, 24 | 23 | 24 | 24 | 23 |
| 2 | 40, 40 | 37 | 39 | 38 | 39 |
| 3 | 34, 30 | 31 | 32 | 32 | 33 |
| 4 | 40, 38 | 37 | 42 | 37 | 38 |
| 5 | 22, 21 | 21 | 22 | 22 | 21 |
| 6 | 58, 59 | 57 | 57 | 58 | 57 |
| 7 | 74, 75 | 72 | 75 | 76 | 74 |
| 8 | 10, 11 | 10 | 12 | 11 | 11 |

EXAMPLE 3

Further Comparison Studies

In this example a magnetically based separation method was compared with a centrifugation based method. In Table 5, magnetic separation was performed with dextran sulfate/MgCl$_2$ (obtained from DMA) as the precipitating reagent (RDI HDL-M). In magnetically sedimented samples, 0.10 ml combined magnetic particle/precipitating reagent (20 ml magnetic particle slurry/100 ml combined reagent) was added to 0.50 ml of sample and the magnetic field applied 10 minutes later. Total sample cholesterol and total sample triglycerides were determined by standard methods and are shown in mg/dl. All other methods and materials are as described in Example 1.

TABLE 5

| | | | METHOD OF SEPARATION | |
|---|---|---|---|---|
| Patient No. | Total Cholesterol | Tri-glyceride | Centrifugal Separation DMA HDL | Magnetic Separation RDI HDL-M |
| 1 | 196 | 389 | 32 | 35 |
| 2 | 199 | — | 35 | 34 |
| 3 | 163 | — | 39 | 37 |
| 4 | — | — | 40 | 36 |
| 5 | 216 | — | 38 | 35 |
| 6 | 247 | 745 | 32 | 33 |
| 7 | 229 | — | 44 | 42 |
| 8 | 156 | — | 47 | 45 |
| 9 | — | — | 42 | 38 |
| 10 | 245 | — | 65 | 64 |
| 11 | 248 | 79 | 56 | 54 |
| 12 | 226 | 209 | 38 | 36 |
| 13 | — | — | — | 50 |
| 14 | 289 | 157 | 78 | 74 |
| 15 | 257 | 214 | 39 | 38 |
| 16 | 273 | 64 | 54 | 55 |
| 17 | 212 | 135 | 36 | 35 |
| 18 | 238 | 201 | 39 | 39 |
| 19 | 207 | 91 | 63 | 62 |
| 20 | 223 | 195 | 48 | 46 |
| 21 | 265 | 204 | 50 | 48 |
| 22 | 175 | — | 46 | 45 |
| 23 | 239 | 107 | 51 | 50 |
| 24 | 236 | 157 | 47 | 45 |
| 25 | 287 | 206 | 49 | 47 |
| 26 | 215 | 296 | 29 | 29 |
| 27 | 206 | 86 | 56 | 53 |
| 28 | 217 | 330 | 44 | 41 |
| 29 | 197 | 184 | 36 | 33 |
| 30 | 254 | 130 | 51 | 47 |
| 31 | 377 | 1,348 | 20 | 31 |
| 32 | 193 | — | 59 | 57 |
| 33 | 97 | — | 34 | 32 |
| 34 | 156 | — | 19 | 19 |
| 35 | 125 | — | 57 | 58 |
| 36 | 204 | — | 37 | 38 |
| 37 | 270 | — | 38 | 39 |
| 38 | 201 | — | 58 | 59 |
| 39 | 203 | — | 64 | 65 |
| 40 | 240 | — | 37 | 38 |
| 41 | 297 | 348 | 47 | 48 |
| 42 | 261 | — | 33 | 35 |
| 43 | 243 | — | 57 | 57 |
| 44 | 103 | — | 45 | 45 |
| 45 | 167 | — | 28 | 29 |
| 46 | 180 | — | 58 | 57 |
| 47 | 208 | 386 | 36 | 29 |
| 48 | 99 | — | 47 | 46 |
| 49 | 280 | — | 71 | 68 |
| 50 | 156 | — | 44 | 44 |
| 51 | 328 | — | 39 | 38 |
| 52 | 216 | — | 70 | 71 |
| 53 | — | | 35 | 35 |
| 54 | 213 | — | 46 | 47 |
| 55 | 205 | — | 45 | 44 |
| 56 | 200 | — | 52 | 51 |
| 57 | 169 | — | 44 | 43 |
| 58 | 312 | — | 47 | 46 |
| 59 | 242 | — | 47 | 47 |

The experiments described in Table 6 are similar to those described in Table 5 except that the dextran sulfate precipitating reagent used in the magnetically based method was not purchased from DMA but was formulated from commercially available dextran sulfate, as described above.

TABLE 6

| | | | METHOD OF SEPARATION | |
|---|---|---|---|---|
| Patient No. | Total Cholesterol | Tri-glyceride | Centrifugal Separation DMA HDL | Magnetic Separation RDI HDL-M |
| 1 | 251 | 176 | 42 | 42 |
| 2 | 246 | 54 | 69 | 67 |
| 3 | 276 | 110 | 55 | 55 |
| 4 | 201 | 120 | 41 | 40 |
| 5 | 234 | 141 | 37 | 36 |
| 6 | 269 | 321 | 43 | 43 |
| 7 | 213 | 379 | 34 | 34 |
| 8 | 180 | 66 | 51 | 48 |
| 9 | 268 | 78 | 56 | 54 |
| 10 | 252 | 115 | 53 | 51 |
| 11 | 254 | 138 | 63 | 60 |
| 12 | 217 | 89 | 62 | 60 |
| 13 | 208 | 140 | 48 | 49 |
| 14 | 185 | 103 | 35 | 34 |
| 15 | 245 | 323 | 39 | 37 |
| 16 | 138 | 77 | 34 | 36 |
| 17 | 245 | 113 | 50 | 52 |
| 18 | 268 | 143 | 56 | 54 |
| 19 | 193 | 277 | 39 | 36 |
| 20 | 177 | 79 | 47 | 39 |
| 21 | — | — | 40 | 39 |
| 22 | 191 | 90 | 56 | 53 |
| 23 | 209 | 335 | 35 | 31 |
| 24 | 231 | 62 | 79 | 77 |
| 25 | 197 | 55 | 68 | 65 |
| 26 | 191 | 90 | 55 | 52 |
| 27 | 205 | 335 | 33 | 31 |
| 28 | 185 | 117 | 50 | 48 |
| 29 | 252 | 117 | 57 | 54 |
| 30 | 220 | 90 | 51 | 48 |
| 31 | 266 | 90 | 54 | 54 |
| 32 | 240 | 157 | 52 | 51 |
| 33 | 198 | 397 | 36 | 37 |
| 34 | 260 | 118 | 56 | 55 |
| 35 | 102 | 96 | 45 | 41 |

TABLE 6-continued

| Patient No. | Total Cholesterol | Tri-glyceride | METHOD OF SEPARATION | |
|---|---|---|---|---|
| | | | Centrifugal Separation DMA HDL | Magnetic Separation RDI HDL-M |
| 36 | 202 | 159 | 56 | 55 |
| 37 | 178 | 79 | 41 | 42 |
| 38 | 171 | 121 | 42 | 41 |
| 39 | 284 | 96 | 86 | 84 |
| 40 | 298 | 169 | 49 | 49 |
| 41 | 167 | 90 | 63 | 61 |
| 42 | 142 | 104 | 25 | 8 |
| 43 | 167 | 118 | 32 | 32 |
| 44 | 136 | 108 | 32 | 33 |
| 45 | 196 | 82 | 58 | 59 |
| 46 | 94 | 40 | 38 | 39 |
| 47 | 157 | 177 | 31 | 31 |
| 48 | 160 | 75 | 47 | 49 |
| 49 | 108 | 61 | 34 | 35 |
| 50 | 149 | 70 | 30 | 32 |
| 51 | 217 | 216 | 40 | 39 |
| 52 | 152 | 89 | 43 | 42 |
| 53 | 212 | 167 | 52 | 51 |
| 54 | 234 | 239 | 44 | 67 |
| 55 | 145 | 100 | 26 | 28 |
| 56 | 184 | 152 | 55 | 50 |
| 57 | 105 | 86 | 31 | 31 |
| 58 | 208 | 148 | 64 | 61 |
| 59 | 147 | 99 | 29 | 30 |
| 60 | 104 | 71 | 47 | 48 |
| 61 | 272 | 159 | 57 | 59 |
| 62 | 247 | 194 | 54 | 55 |
| 63 | 251 | 167 | 59 | 60 |
| 64 | 347 | 742 | 34 | 34 |
| 65 | 274 | 242 | 39 | 40 |
| 66 | 168 | 66 | 76 | 74 |
| 67 | 286 | 275 | 31 | 31 |
| 68 | 212 | 123 | 35 | 36 |
| 69 | 190 | 134 | 50 | 50 |
| 70 | 271 | 343 | 35 | 35 |
| 71 | 233 | 380 | 34 | 34 |
| 72 | 271 | 182 | 58 | 57 |
| 73 | 222 | 134 | 31 | 30 |
| 74 | 252 | 271 | 35 | 34 |
| 75 | 240 | 285 | 34 | 33 |
| 76 | 298 | 217 | 37 | 37 |
| 77 | 320 | 254 | 30 | 31 |
| 78 | 186 | 158 | 36 | 34 |
| 79 | 232 | 108 | 59 | 56 |
| 80 | 278 | 127 | 46 | 44 |
| 81 | 281 | 136 | 49 | 49 |
| 82 | 240 | 62 | 56 | 55 |
| 83 | 231 | 124 | 50 | 47 |
| 84 | 281 | 80 | 64 | 60 |
| 85 | 269 | 269 | 63 | 55 |
| 86 | 214 | 112 | 42 | 39 |
| 87 | 251 | 109 | 51 | 48 |

Table 7 compares the effect of waiting 1 minute or 10 minutes after addition of the combined magnetic particle/precipitating reagent before applying the magnetic field. Other conditions were as described for Table 6.

TABLE 7

| Patient No. | Total Cholesterol | Tri-glyceride | METHOD OF SEPARATION | | |
|---|---|---|---|---|---|
| | | | Centrifugal Separation DMA HDL | Magnetic Separation | |
| | | | | RDI HDL-M (10 min) | RDI HDL-M (1 min) |
| 88 | 283 | 124 | 52 | 51 | 52 |
| 89 | 215 | 88 | 42 | 42 | 44 |
| 90 | 221 | 191 | 34 | 34 | 35 |
| 91 | 254 | 457 | 42 | 42 | 41 |
| 92 | 259 | 164 | 45 | 46 | 47 |
| 93 | 284 | 152 | 40 | 39 | 40 |
| 94 | 225 | 155 | 45 | 44 | 46 |
| 95 | 276 | 343 | 31 | 31 | 31 |
| 96 | 228 | 277 | 37 | 36 | 37 |
| 97 | 207 | 202 | 38 | 37 | 39 |
| 98 | 256 | 285 | 48 | 46 | 48 |
| 99 | 209 | 264 | 36 | 35 | 36 |
| 100 | 209 | 503 | 46 | 45 | 42 |
| 101 | 169 | 175 | 28 | 27 | 30 |
| 102 | 119 | 100 | 30 | 31 | 32 |
| 103 | 124 | 101 | 22 | 21 | 23 |
| 104 | 118 | 105 | 26 | 26 | 27 |
| 105 | 93 | 53 | 37 | 39 | 40 |
| 106 | 111 | 54 | 38 | 38 | 40 |
| 107 | 194 | 203 | 33 | 32 | 34 |
| 108 | 231 | 298 | 57 | 45 | 46 |
| 109 | 205 | 118 | 75 | 73 | 75 |
| 110 | 184 | 223 | 31 | 32 | 33 |
| 111 | 127 | 106 | 32 | 32 | 33 |
| 112 | 158 | 73 | 41 | 41 | 41 |
| 113 | 208 | 222 | 33 | 32 | 32 |
| 114 | 273 | 326 | 26 | 25 | — |
| 115 | 149 | 65 | 23 | 24 | 23 |
| 116 | 239 | 132 | 35 | 34 | 36 |
| 117 | 247 | 154 | 47 | 49 | 47 |
| 118 | 266 | 136 | 39 | 38 | 38 |
| 119 | 215 | 182 | 46 | 44 | 46 |
| 120 | 268 | 174 | 43 | 42 | 43 |

EXAMPLE 4

Magnetically Responsive Particle-Based Clinical Assay for HDL Cholesterol

The precipitating reagents dextran sulfate and MgCl, together, precipitate LDL and VLDL in serum. In this assay magnetically responsive particles, preferably polyacrolein-iron particles (polyacrolein:iron oxide ($Fe_3O_4$)=40:60) 1–10 $\mu$ in diameter and the precipitating reagents are added to the sample simultaneously. After precipitation, the LDL and VLDL are pelleted by the application of a magnetic field to the sample. HDL remains in the supernatant. The amount of HDL cholesterol is then assayed using an enzymatic reagent that measures total cholesterol. The intensity of color produced in the reaction is proportional to the concentration of HDL cholesterol. The assay is described in detail below.

The preferred sample is serum, though EDTA plasma may be used. The sample need not be fasting. Plasma (or serum) should be separated from the erythrocytes as soon as possible after collection since various changes can occur during storage. HDL cholesterol in plasma samples is stable for at least four days at 4°–8° C. or up to 2 weeks at −20° C.

Precipitation and fractionation are performed as follows:

a. Dispense 0.50 mL of each serum sample and control into an appropriately labeled test tube;
b. Add 0.10 mL of combined magnetic particles/precipitating reagent (dextran sulfate (0.1 mmol/l)), $MgCl_2$ (250 mmol/l), and magnetically responsive particles (10 g/l) to the sample and vortex immediately for 10 seconds;
c. Incubate 1–10 minutes at 15°–30° C.;
d. Place the tubes on a magnetic surface and wait approximately 3 minutes for complete sedimentation of the magnetically responsive particles.

Longer sedimentation times may be necessary if the sample has a high level of triglycerides (see below). In any case, the sedimentation time can be established by methods known to those skilled in the art. The assays are performed in 10×75 mm or 12×75 mm round bottom test tubes. Round bottom tubes are preferable to tubes with pointed or tapered bottoms because round bottom tubes result in a larger proportion of the sample being held more closely to the source of magnetism. The tubes are placed in racks that contain magnets in the base of the rack. Magnetic racks suitable for use in methods of the invention are available through: Serono Diagnostics, Allentown, Pa.; Gen-Probe, Inc., San Diego, Calif.; Ciba-Corning Diagnostics, E. Walpole, Mass.; Advanced Magnetics, Inc., Cambridge, Mass.; and Amersham Corp., Arlington Hts., Ill.. A suitable rack exerts a magnetic flux density of approximately 175 to 265 gauss 0.5 inch from the surface upon which the bottom of the sample tube rests.

e. Obtain an aliquot of clear supernatant for the cholesterol assay by transferring the supernatant solution to a second labeled test tube for analysis. HDL cholesterol in the supernatant is stable for at least 72 hours when stored at 2°-8° C.

f. Determine cholesterol content with a cholesterol identifying agent, e.g., with the DMA Enzymatic Cholesterol Reagent Set (DMA Cat. No. 2340). Measurements can be converted to cholesterol concentration by comparison to known calibrators, using e.g., the DMA HDL cholesterol standard (DMA Cat. No. 2331-153).

g. Due to dilution of the sample during the precipitation step, multiply the HDL cholesterol concentration by 1.2 to obtain the final result.

Expected values for HDL are typically in the range of 30-70 mg/dL in males and 30-85 mg/dL in females. Each laboratory, however, should establish its own range of expected values.

Determination of HDL-Cholesterol in Samples With High Levels of Triglycerides

Many precipitating reagents and sedimentation methods are not suitable for use with samples which contain high levels of triglycerides (greater than about 300-500 mg/dl) when centrifugation is used for sedimentation in that the supernatant is cloudy or turbid after precipitation and centrifugation. In these cases, samples with high levels of triglycerides must be diluted prior to precipitation to avoid erroneous cholesterol determinations. Methods of the invention, however, can be used on samples with triglyceride levels as high as 1000-1300 mg/dl, without dilution of the samples, although high triglyceride samples may require slightly longer sedimentation times than are used with normal samples.

Other embodiments are within the claims.

What is claimed is:

1. A combined reagent for separating lipoproteins comprising a selective chemical precipitating reagent and a magnetically responsive particle, said selective chemical precipitating reagent being present, in said combined reagent, at a concentration sufficient to precipitate a lipoprotein, and wherein if said selective chemical precipitating reagent is polyanionic, then a divalent cation is included.

2. The combined reagent of claim 1, wherein said selective chemical precipitating reagent comprises dextran sulfate and $Mg^{++}$.

3. The combined reagent of claim 1, wherein said selective chemical precipitating reagent comprises phosphotungstic acid and $Mg^{++}$.

4. The combined reagent of claim 1, wherein said selective chemical precipitating reagent comprises heparin and $Ca^{++}$ or $Mn^{++}$.

5. The combined reagent of claim 1, wherein said selective chemical precipitating reagent comprises polyethyleneglycol.

6. The combined reagent of claim 1, wherein said selective chemical precipitating reagent comprises polyvinyl sulfate and polyethyleneglycol.

7. A combined reagent for separating lipoproteins comprising a selective chemical precipitating reagent and a magnetically responsive particle, said selective chemical precipitating reagent being present, in said combined reagent, at a concentration sufficient to precipitate a lipoprotein, said magnetically responsive particle having a particle diameter of approximately 1-10 micrometers, and wherein if said selective chemical precipitating reagent is polyanionic, then a divalent cation is included.

8. The combined reagent of claim 7, wherein said selective chemical precipitating reagent comprises dextran sulfate and $Mg^{++}$.

9. The combined reagent of claim 7, wherein said selective chemical precipitating reagent comprises phosphotungstic acid and $Mg^{++}$.

10. The combined reagent of claim 7, wherein said selective chemical precipitating reagent comprises heparin and $Ca^{++}$ or $Mn^{++}$.

11. The combined reagent of claim 7, wherein said selective chemical precipitating reagent comprises polyethyleneglycol.

12. The combined reagent of claim 7, wherein said selective chemical precipitating reagent comprises polyvinyl sulfate and polyethylene glycol.

13. A combined reagent for separating lipoproteins comprising a selective chemical precipitating reagent and a magnetically responsive particle, said selective chemical precipitating reagent being present, in said combined reagent, at a concentration sufficient to precipitate a lipoprotein, and wherein said magnetically responsive particles are present in said combined reagent at a concentration of 5-50 milligrams per milliliter.

14. The combined reagent of claim 13, wherein said selective chemical precipitating reagent comprises dextran sulfate and $Mg^{++}$.

15. The combined reagent of claim 13, wherein said selective chemical precipitating reagent comprises phosphotungstic acid and $Mg^{++}$.

16. The combined reagent of claim 13, wherein said selective chemical precipitating reagent comprises heparin and $C^{++}$ or $Ms^{++}$.

17. The combined reagent of claim 13, wherein said selective chemical precipitating reagent comprises polyethyleneglycol.

18. The combined reagent of claim 13, wherein said selective chemical precipitating reagent comprises polyvinyl sulfate gild polyethyleneglycol.

19. The combined reagent of claim 13, wherein the concentration of said magnetically responsive particles is 15-25 milligrams per milliliter.

* * * * *